(12) United States Patent
Krattiger

(10) Patent No.: US 7,486,805 B2
(45) Date of Patent: Feb. 3, 2009

(54) METHOD AND OPTICAL SYSTEM FOR MEASURING THE TOPOGRAPHY OF A TEST OBJECT

(75) Inventor: Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 442 days.

(21) Appl. No.: 11/212,886

(22) Filed: Aug. 26, 2005

(65) Prior Publication Data

US 2006/0055942 A1 Mar. 16, 2006

Related U.S. Application Data

(63) Continuation of application No. PCT/EP2004/001290, filed on Feb. 12, 2004.

(30) Foreign Application Priority Data

Feb. 27, 2003 (DE) ................. 103 08 383

(51) Int. Cl.
*G06K 9/00* (2006.01)
*G01B 11/24* (2006.01)
(52) U.S. Cl. .................. 382/108; 382/128; 356/603
(58) Field of Classification Search .......... None
See application file for complete search history.

(56) References Cited

U.S. PATENT DOCUMENTS

| | | | |
|---|---|---|---|
| 4,986,262 A | 1/1991 | Saito ................ | 128/6 |
| 5,090,400 A | 2/1992 | Saito ................ | 128/6 |
| 5,150,254 A | 9/1992 | Saitou ............... | 359/367 |
| 5,669,871 A | 9/1997 | Sakiyama ........... | 600/117 |

FOREIGN PATENT DOCUMENTS

| | | |
|---|---|---|
| DE | 35 16 164 C2 | 11/1985 |
| DE | 44 10 134 A1 | 9/1994 |
| DE | 196 04 977 A1 | 8/1997 |
| DE | 19604977 A1 | 8/1997 |
| JP | 2002-17729 * | 1/2002 |
| JP | 2002257527 | 9/2002 |
| WO | WO 93/03579 | 2/1993 |

OTHER PUBLICATIONS

International Preliminary Report; Feb. 23, 2006; 9 pages.
Machine Vision News, vol. 4 1999.
3D Measurement Endoscope, K. Armbruster and M. Scheffler dated Feb. 14, 2002.
International Search Report dated Jun. 11, 2004.

* cited by examiner

*Primary Examiner*—Bhavesh M Mehta
*Assistant Examiner*—Charles Kim
(74) *Attorney, Agent, or Firm*—St. Onge Steward Johnston & Reens LLC

(57) ABSTRACT

Disclosed is an optical system for measuring the topography of a test object, comprising a system for projecting an optically recognizable test pattern onto the surface of an object area that is to be measured, and an image-recording system and image-evaluation system for determining the parallactically displaced image coordinates of the test pattern in the object area that is to be measured, the distance of the centers of the aperture diaphragms of the projection system and the image-recording system forming a test basis. Said optical system is characterized in that the test pattern consists of a limited number of elements that are placed at regular intervals in at least one first axial direction, said axial direction being rotated by an angle a relative to the vertical projection of the test basis.

29 Claims, 7 Drawing Sheets

METHOD AND OPTICAL SYSTEM FOR MEASURING THE TOPOGRAPHY OF A TEST OBJECT

This application is a continuation of pending international patent application PCT/EP2004/001290 filed on Feb. 12, 2004 which designates the United States and claims priority of German Application No. 103 08 383.9 filed on Feb. 27, 2003.

FIELD OF THE INVENTION

The invention relates to a method and optical system for measuring the topography of a test object, having the characteristics disclosed in the generic portion of Patent Claim 1, and an optical system appropriate to said method, having the characteristics cited in the generic portion of Patent Claim 6.

Optical measurement systems, which obtain a number of spatial coordinates of the surface of a test object by parallactically projecting complex patterns onto an object, exist in the state of the art. In general in such cases a regular striped pattern is projected onto the test object. The position of the stripes is recorded with a scanner or a video camera. The measuring is based on a triangulation, so that the projection and image-recording angle and the distance between the camera and projector must be known. Because the stripes are not identifiable individually, there results a modulation uncertainty in determining the spatial coordinates, and said uncertainty must be resolved through multiple recordings, each at various stripe distances.

The projection of regular point patterns, which are produced by laser illumination of a diffractive optical element, is also part of the state of the art in automatic object recognition. A paper in *Machine Vision News*, Vol. 4, (1999) describes the displacement of the elements of a regular point pattern on projection onto an uneven surface. It is stated in general that new possibilities of object recognition would be opened up as a result, without any more precise description of these possibilities such as an identification of the points of the surface.

To exclude modular uncertainties in the optical measurement of spatial structures, unequivocally identifiable measurement data are mainly used, which are applied on the test object. With the help of image-recording and image-evaluating systems, these measurement data can be individually recognized and measured.

Measurement of three-dimensional structures or of surfaces and lengths is also a matter of significance in endoscopic measurement technology.

In medical applications, for instance, the minimally invasive recognition of shapes and volumes of tumors is important as an aid in decision making for the optimal treatment or for monitoring the growth process.

In technical endoscopy, for instance, on the basis of a quantitatively determined material error, it is possible to avoid or postpone the dismantling of the device until a critical mass is determined.

In these applications it is impossible to apply special measurement data on the test object.

Besides other measurement methods, therefore, in measurement endoscopy as well, use was made of the principle of image evaluation of the parallax, that is, of the apparent lateral displacement of an illuminated pattern, depending on the projection distance. In a 3D measurement endoscope described by K. Armbruster and M. Scheffler, of the Institut für angewandte Forschung in der Automation, in FH Reutlingen, structured light, for example a line pattern is projected into the object space that is to be measured and the setting image is photographed with a camera from a second perspective. In this method the position of the light source is defined with respect to the camera so that the 3D coordinates of an object surface can be calculated by means of triangulation. A method for photographing and measuring bodies was presented by K. Armbruster in the Volume of Proceedings of the $3^{rd}$ Symposium on Image Processing, Technical Academy, Esslingen (1993).

In U.S. Pat. No. 5,150,254 A1 the principle of shape recognition by evaluation of a projected marker line was described in general terms. Stabilization of the angle of projection and the position of the marker line were cited as a fundamental problem, because both are decisive for the exact determination of the distance to the test object. The angle of projection and the image-recording angle are selected in such a way that the marker line lies in the middle of the image.

U.S. Pat. No. 5,669,871 A1 describes an endoscope with an illuminating system positioned on its distal end, a CCD image-recording system and a projection system for a line of reference. The optical axes of the image-recording system and of the projection system are at a defined distance from one another. A single line of reference is projected onto the object plane, so that the projection system has a means of adjustment in order to produce the straightest possible line of reference. In cylindrically domed object surfaces, the endoscope must be oriented in such a way that the line of reference runs parallel to the cylindrical axis. In addition it is essential in each case to ensure that the line of reference lies on the object part that is to be measured.

Through image evaluation, the spatial coordinates of a straight line are calculated for the lines of reference superimposed on the object image and the straight line is close to the image of the projected line of reference. From the deformations of the line of reference in the object image relative to the calculated straight line, the spatial coordinates of selected object points situated on the straight line of reference can be determined Patent DE 3516164 C2 descries a system for optical length measurement with an endoscope. On the distal end of the endoscope, a projection system and an image-recording system are positioned at a fixed distance from one another. The optical axes of the two systems are arranged parallel to one another and the angles of aperture of the projection of the projection cone and of the image-recording cone are equal. By means of the projection system, a circular marker, for instance, is projected onto the object and is depicted in the image of the test object. The distance of the circular marker from the uppermost point of the visual field constitutes a reference length whose size is independent of the respective object distance because the parallactic displacement of the boundary of the visual field and of the position of the circular marker run parallel to one another, because of the equal conic angle.

Only one length estimation is possible with this method by means of relative length comparison. The exactitude depends, moreover, on whether the boundary of the visual field and the projection of the circular marker are situated in the same plane. No information can be obtained on heights by means of the test object.

It is therefore the object of the invention to produce a method of measurement and a system of measurement on the basis of illuminated measurement data for parallactic determination of coordinates, so that with the help of an image-evaluation system an unequivocal identification of the measurement data can be achieved entirely from the position of the measurement data in the image of the test object and the measuring system is not required to be situated so that it is adjusted to the shape of the test object.

This object is fulfilled according to the invention through a method of the aforementioned type having the defining characteristics of Patent Claim 1. Advantageous refinements are obtained from the characteristics of related Claims 2 through 5.

An optical system of the aforementioned type, appropriate for fulfilling the object, has, according to the invention, the defining characteristics of Claim 6. Advantageous embodiments are derived from related Claims 7 through 26.

The optical system, according to Claim 27, is particularly appropriate for use in an endoscope. An advantageous embodiment results from the defining characteristics of related Claim 28.

The fundamental concept in the invention consists in the fact that the first axis for positioning the elements of the test pattern is inclined by an angle ac relative to the vertical projection of the base line into a plane of reference. The base line is thus the connecting line between the midpoints of the pupils of the projection and image-recording system. The plane of reference is vertical to the optical axis of the image-recording system in the object space removed from the distal end of the optical system by a reference distance. It is the surface in which the test pattern is defined with the system parameters (x, a, s, t, n, m) explained in further detail hereafter. By establishing the reference distance, the distance-dependent parameters s and t receive a fixed value. The reference distance can be selected to be, for instance, the middle working distance for which the optical system is designed.

In a one-dimensional test pattern, only the inclination at a selected angle of 0 0 degrees ensures that with the parallactic displacement of the elements of the test pattern every element moves on its own line of displacement parallel to the projection of the base line. For an unequivocal proof of every element in the image, however, the size of the element and the dissolution power of the image-recording system must be considered in selecting the angle. At too small an angle oc, otherwise, neighboring elements could partly be covered up because of the resulting strongly differing parallactic displacement, with great local differences of height in the test object. The angle a should therefore be selected so that the distance a between the lines of displacement of every element is great enough so that sufficient space remains to the neighboring element for the surface of every element even with an error value of the position and with a possibly distorted line of displacement.

In a two-dimensional test pattern, the second axis can be inclined for the alignment of the other elements at any desired ankle beta relative to the first axis. Even here, however, care must be exercised so that with the parallactic displacement of the bar elements no mutual covering of the lines of displacement can occur. Depending on the number n and the distance s of the elements along the first axial direction and the distance t of the elements along the second axial direction, the angle a=arc tan 1n~1s~1 has proven to be optimal. It corresponds to a distance 1 of the lines of displacement in the size of a=ts(n2s2+t2)~½ sin β (beta). Hereafter, for simplicity's sake, a right angle is most often assumed between the two axes.

With the regular arrangement of the elements of the test pattern, as defined by the parameters s and t, care must be exercised so that manufacturing tolerances of the generating optical component and illustration errors of the projection system can cause distortions of the test pattern in the plane of reference that can result in slightly distorted connecting lines in the axial directions, rows of lines, and column lines of the elements. In the plane of reference, therefore, the elements of the test pattern can differ from the pre-established regularity by an uncertainty u. To ensure identifiability of the elements of the test pattern according to the invention, the uncertainty u should be less than half the distance a of the lines of displacement of the regular test pattern. Therefore, u<½ts(n2s2+t2)–½ should apply. By respecting this condition, the lines of displacement have no common points despite a distortion.

To produce the test pattern it is useful to use a diffractive optical element (DOE) that is illuminated with a diode laser. A DOE works at relatively low loss rates and is easily handled in installation in the optical system to achieve the necessary orientation of the projected test pattern. With a test pattern with point-shaped elements, they can be produced with high intensity and sharp concentration.

The pre-established limitation of the number of elements along each axial direction ensures that all elements depicted in the image plane can be completely identified. The situation of the identified elements can be compared, in image processing, with the corresponding positions in the calibration images.

Any possible absent elements have no influence on the identifiability of the other elements.

From the image coordinators of the elements in the image of the test object determined through image processing, the related spatial coordinates of the element can be determined in the test pattern on the test object. The elements identified with their spatial coordinates can then be used as supports for calculating a surface adapted to it. Mathematical methods for computing fitted surfaces are known in the state of the art in their own right and in particular also allow a correlation with corresponding data sets from surface shapes acquired elsewhere.

In the illustration, embodiments of the invention are presented schematically and are described in greater detail on the basis of the drawings.

DETAILED DESCRIPTION OF PREFERRED EMBODIMENTS

Figure 1:
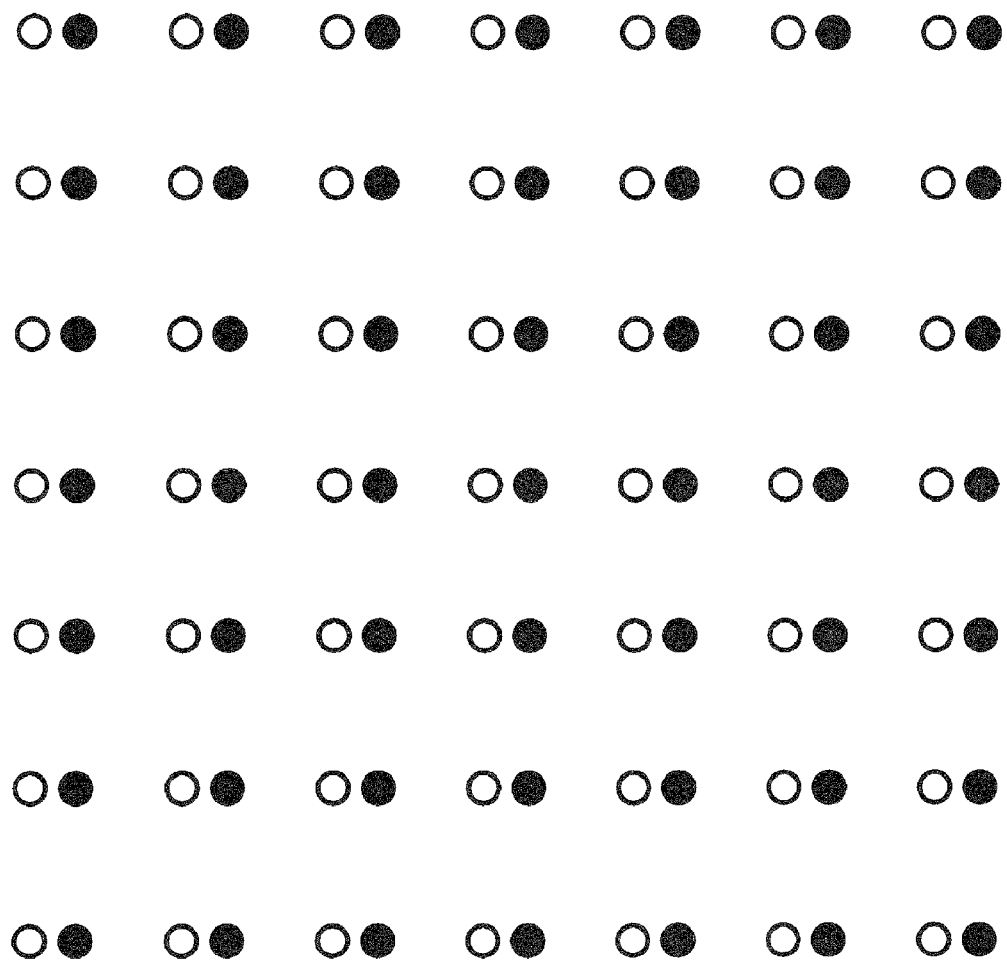
FIG. 1 shows the parallactic displacement of a point pattern with small changes in distance of a plane surface.

FIG. 1 illustrates the principle of parallactic displacement of a point pattern. The filled-in points represent the position of the point pattern on a calibration object in a certain projection plane. If the distance to this plane is modified only slightly, the point pattern in the image at first proximity describes a lateral displacement parallel to a connecting line between the midpoints of the output pupil of a projection system and the entry pupil of an image-recording system.

This connecting line forms the base of the measurement system. With a minor change of distance, the parallactic displacement of the point pattern is also minor; as is made clear from the points represented as rings. In this case each ring can be clearly related to its starting position.

Figure 2:
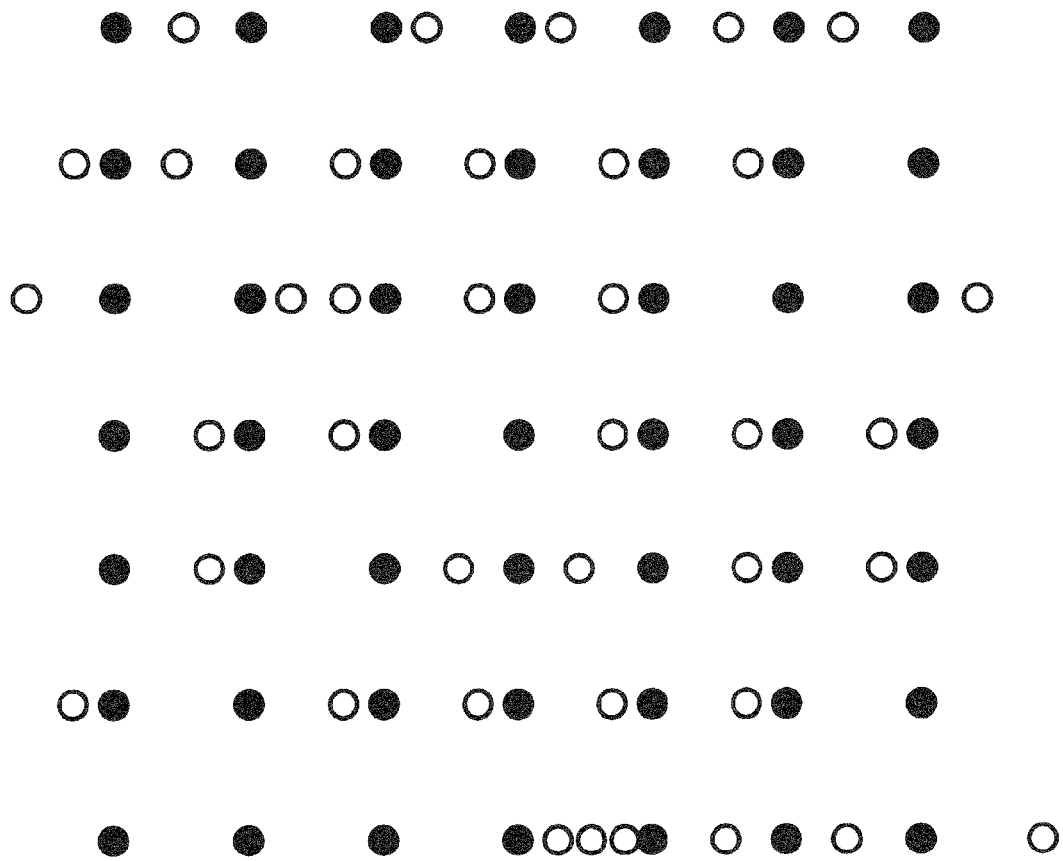
FIG. 2 shows the parallactic displacement of a point pattern between a plane surface and a body with great height differences.

FIG. 2 shows the parallactic displacement of the point pattern with projection onto a test object with a topography that clearly lies above and below the plane of the calibration object. The filled-in points in turn represent the position of the point pattern on the calibration object in a certain projection distance.

The points depicted as rings appear in the image of the test object and are recognizably not related to any particular starting position. An unequivocal determination of the spatial coordinates of the illuminated points is not possible, especially when individual points are still not present in the image.

Figure 3:
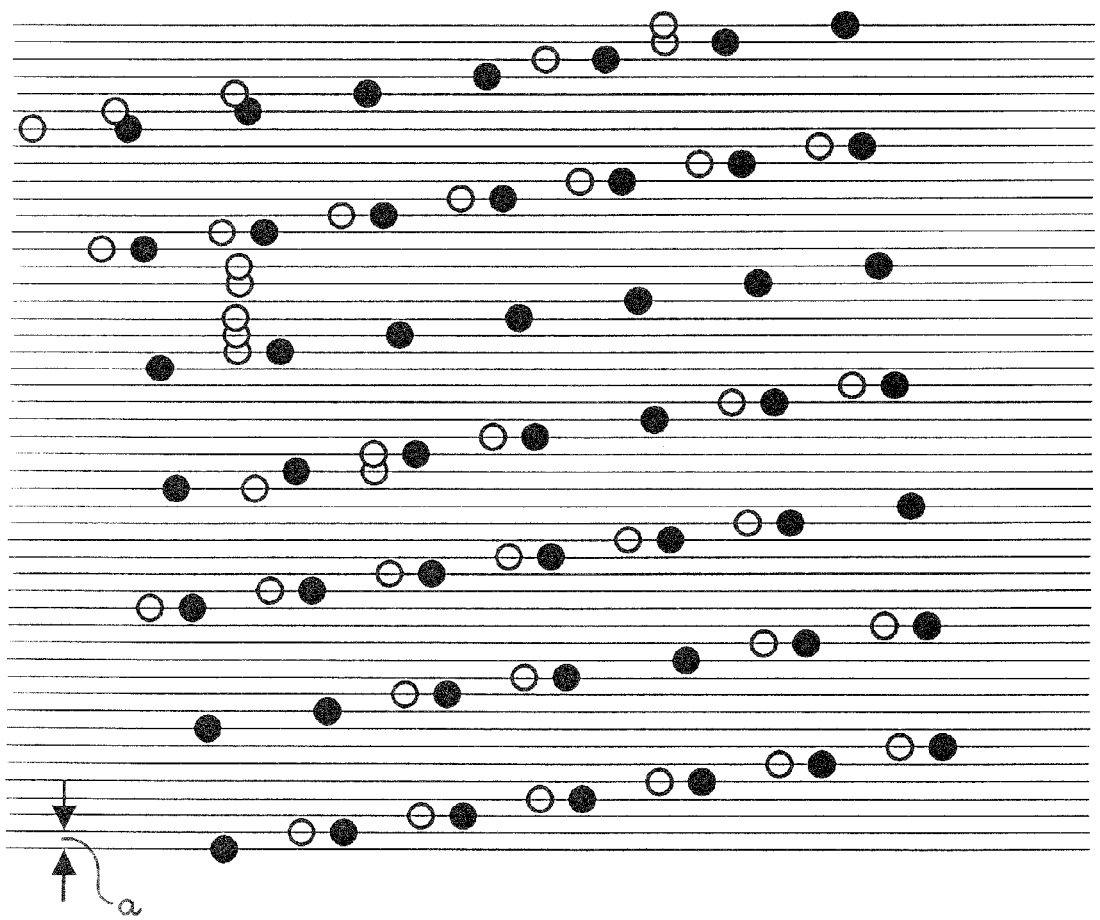
FIG. 3 shows the parallactic displacement with inventive arrangement of a point pattern.

FIG. 3 shows a point pattern in the inventive position.

The depicted lines run parallel to the base of the measurement system.

The axial directions for the point pattern run at an angle to these lines. The result is a distance between the lines, whereby each of the filled-in points, upon its parallactic displacement, runs along its own line on which no additional points lie. The parallactically displaced points depicted as rings are also still separately recognizable despite partial overlapping and can be related to their respective starting position.

Even absent points in the parallactically displaced image do not disturb the evaluation of the additional points.

Figure 4:
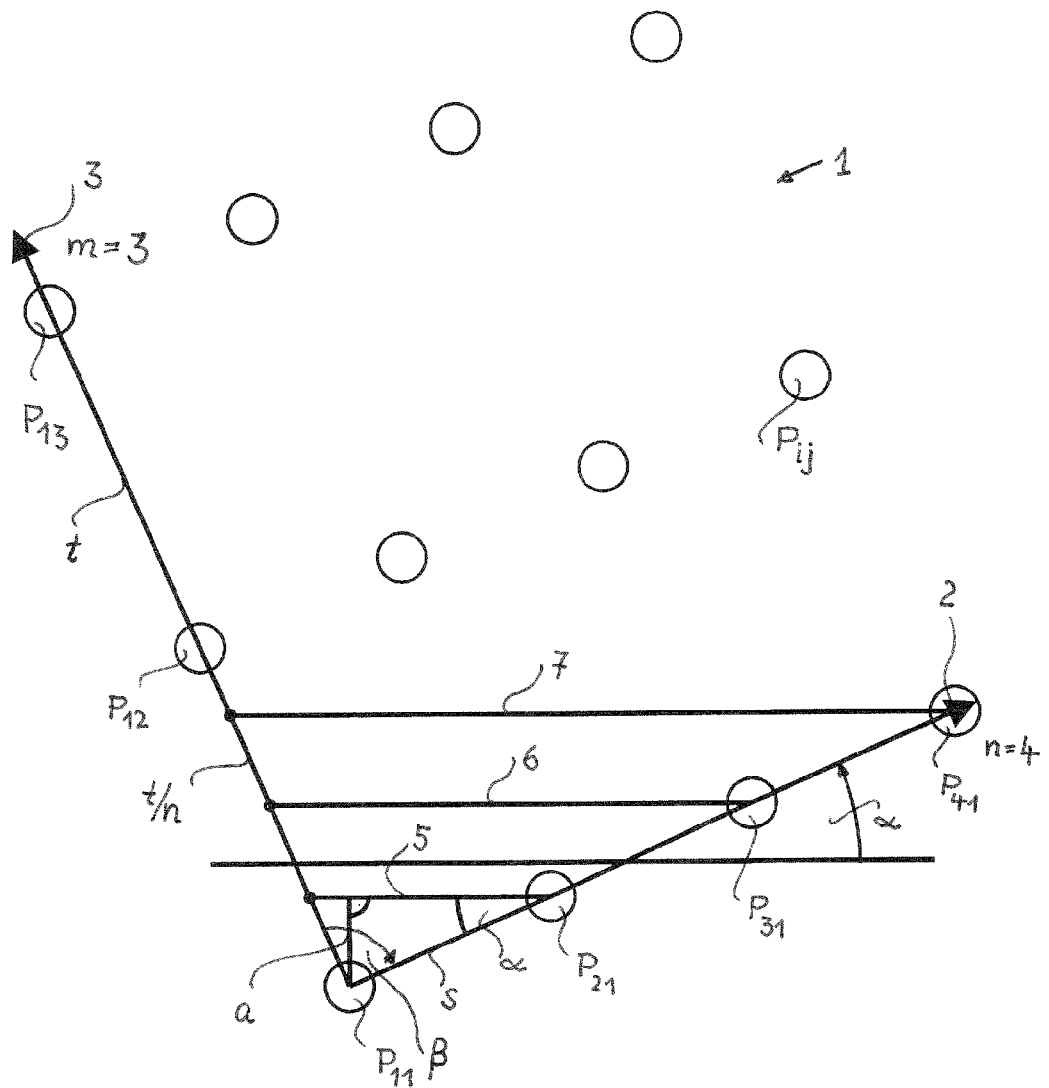
FIG. 4 shows the geometric conditions for the arrangement of the inventive point pattern in a place of reference.

FIG. 4 shows a test pattern 1 consisting of elements $P_{ij}$ (i=1, ..., n; j=1, ..., m) projected onto a reference plane. In a first axial direction 2, n=4 elements are arranged at regular intervals to one another. In a second axial direction 3, m=3 elements are arranged at regular intervals to one another. The axial direction 2 is rotated by an angle alpha relative to the vertical projection of the base 4. The axial direction 3 in this example is situated vertically on the axial direction 2; that is, beta=30 degrees. The angle alpha is selected in such a way that no additional elements $P_{ii}$ lie on the lines of displacement 5, 6, 7 of the elements $P_{21}$, $P_{31}$, $P_{41}$. The related distance a between the lines of displacement 5, 6, 7.

The related distance a between the lines of displacement 5, 6, 7 is derived from $a = ts(n2s2+t2)-\frac{1}{2} \sin \beta$. The optimal angle alpha is $\alpha = \arctan t \cdot n^{-1} \cdot s^{-1}$, where t/n is the size of the axial segments on the axial direction 3, which derive from the crossing points of the lines of displacement 5, 6, 7 with the axial direction 3. Unequivocal identification of the elements $P_{ij}$ in the image of the test object is thus ensured. The depicted content is based on an ideal system. In practice the projection system 8 can produce distortions of the position of the $P_{ij}$.

Figure 5:
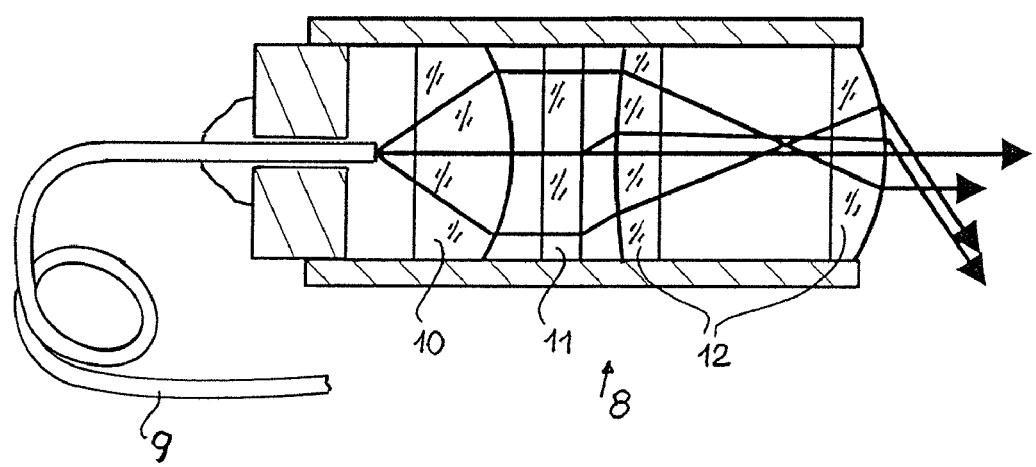
FIG. 5 shows a projection system to produce a point pattern.

FIG. 5 shows a projection system 8 to produce the test pattern 1. The projection system 8 is supplied with light by a glass fiber 9. The light arrives by way of an aspherical collimation lens 10, for instance. After collimation, the light consists of even waves, which go through a diffractive optical element (DOB) 11. This element splits the single collimated, entering light beam into many partial beams, which then produce the previously described test pattern with the elements $P_{ij}$. Such DOE's are commercially available and can also be manufactured for various element shapes.

In addition to the point pattern, other forms such as a pattern from crossed coordinate lines can also be appropriate, provided the points of intersection move on independent lines of displacement.

Reasons for selecting the regular point pattern are the commercial availability of the DOE, the clear recognizable quality of the pattern because the light capacity is concentrated on small points, and, even with an optical distortion, the still relatively round shape of the points, which can easily be recognized by an automatic image-processing program. The system can essentially also be used with irregular test patterns, as long as every point has its own line of displacement.

Below the DOE a line system 12 can be positioned which adjusts the angle of illumination of the point pattern to the visual field of an image-recording system.

Figure 6:
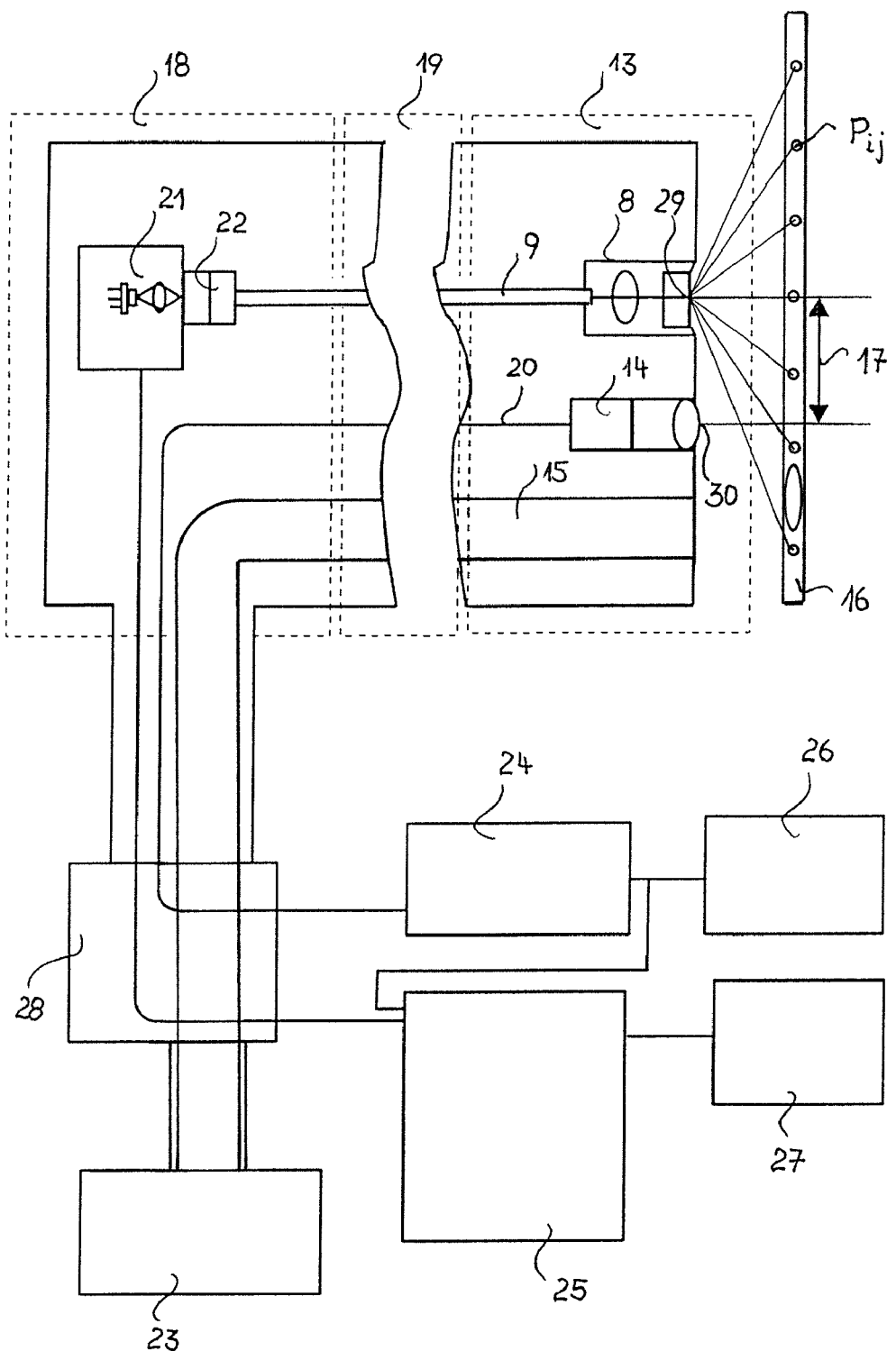
FIG. 6 shows a construction for a test system.

FIG. 6 depicts the components of a complete measurement system into which the inventive optical system is integrated.

The measurement system has a head portion 13, which includes a projection system 8, an image-recording system 14, and a light leader cable 15 to illuminate the test object. The head part can also form the distal end of a video endoscope. The connecting line between the pupil midpoints of the projection system 8 and of the image-recording system 14 forms a test basis 17. The projection system 8 projects a point pattern $P_{ij}$ onto the surface 16 of the test object.

The head part 13 is connected with the operating element 18 of the measurement system by means of a shaft 19. The shaft 19 can also be a rigid or flexible endoscope tube. It contains the fibers 9 for illuminating the projection system 8, the electrical transmission lines 20 from and to the image-recording system 14, and a light leader cable 15.

The glass fiber 9 is fed in the operating element 18 by a laser diode 21.

The fiber type can be selected, depending on the demands, to be multimodal, single-modal, or single-modal-polarization-containing. A removable plug-in connection 22 is provided for greater ease of installation.

The function of the DOE contained in the projection system 8 is based on wavelength-dependent bending effects. The size of the test pattern thus changes in immediate proximity proportionally to the wavelength. To eliminate the resulting measurement uncertainty, the wavelength can either be held constant by thermostatizing the laser diode 21 or the wavelength is recorded by means of a temperature measurement on the laser diode 21 in order to compensate numerically the change in size of the test pattern.

The measurement system described so far is associated with several console appliances. A cold light source 23, for instance, supplies light energy to illuminate the test object by means of the light leader cable 15. The image-recording system 14, for instance, is a video camera with CCD chip which is controlled by a camera controller 24. A computer 25 with its software essentially controls the image recording, image management, image processing, calibration of the measurement system, the execution of the measurement, the control of the laser diode 21, and the temperature measurement and stabilization. A first and a second monitor 26, 27 can be linked up to the camera controller 24 and the computer 25. The connection of the console devices to the service element 18 is done by means of a plug-in distributor 28.

To obtain appropriate measurement values, the laser diode 21 is usefully switched on and off image-synchronously in quick succession. This provides the image-processing software, first of all, with state-of-the-art differentiation formation between successive images with and without test pattern. The differentiation then contains mainly just the image information of the test pattern.

In addition, an image without the disturbing test pattern is available for observation purposes.

The laser diode 21, in addition, can be further modulated in intensity with a noise so that a slight variation in the wavelength arid thus, continuing onward, a fluctuation in the speckle structure is caused. This improves the position determination of the elements of the test pattern and thus the measurement exactitude of the system.

The projection system 8 is positioned beside the image-recording system 14 in the illustrated sectional plane. During installation it is easily rotated so that the orientation of the test pattern to the extent previously described lies slightly diagonal to the projection of the base 17. During image depiction, this leads to the optical effect of an inclined test pattern.

Figure 7:
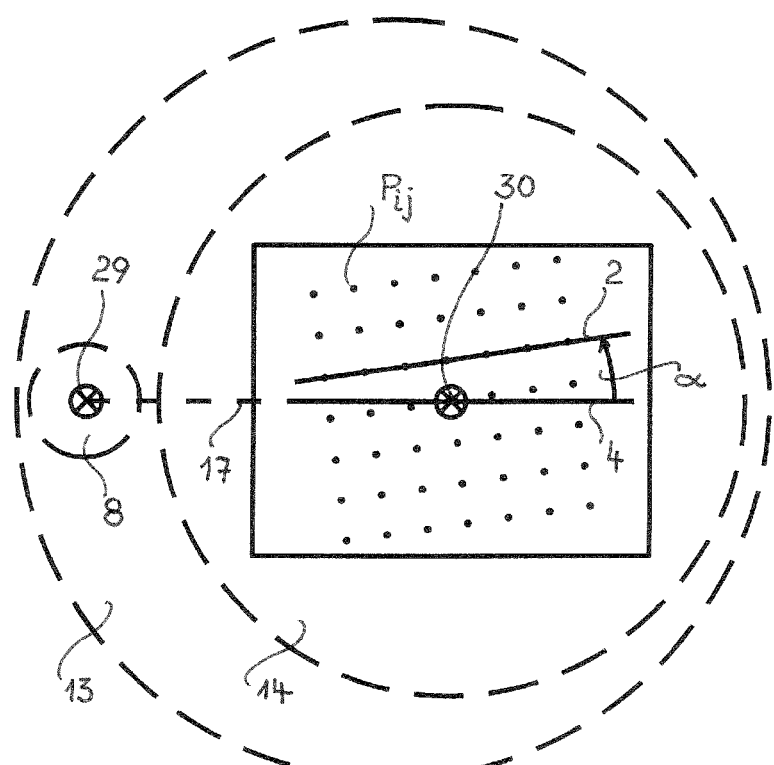
FIG. 7 shows a cross-section through the proximally viewed image plane of the test system.

FIG. 7 shows the section through the image plane in the view with the projected point pattern Pij and the vertical projection 4 of the test basis 17. The test basis 17 in the illustration is the connecting line between the midpoint 29 of the exit pupil of the projection system 8 and the midpoint 30 of the entrance pupil of the image-recording system 14.

Figure 8:
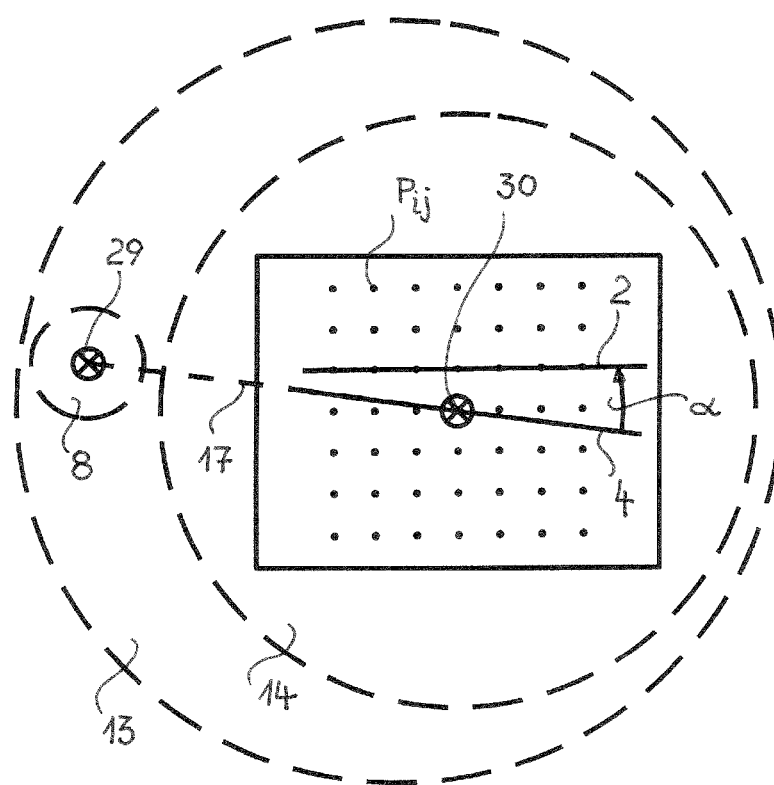
FIG. 8 shows a cross-section through the image plane with a different arrangement of the projection system.

It is possible, however, to position the projection system 8 in such a way that the projection 4 of the test basis runs at an inclined angle to one image side. This special case is illustrated in FIG. 8, with the projection of the test basis forms the angle alpha with one image side. The result is that the first axial direction 2 is directed parallel to an image side, corresponding to a more useful view. Here, however, the lines of displacement run at an inclined angle to the image side.

The parallactically displaced test pattern in the image of the test object can be evaluated basically by two different methods.

The basis of an analytic process consists in determining and storing calibration parameters for every measurement system on the work side with the help of test images. The parameters are: image coordinates of all elements Pij in the selected calibration distance, the basis, the focal distances, the distortion, and the individual centering error of the optics.

In measuring, the measurement system must identify the elements Pij; that is, the indices I, j must be unequivocally determined. With basically familiar mathematical formulas, the spatial coordinates x, y, z are computed from the respective image coordinates u, v on the CCD chip of the video camera.

The basis for an interpolation process is the recording of n calibration images in n calibration distances, where a coordinate grid is used as calibration object. In the calibration image k the elements P(k)jj are identified. For every element P(k)ij the image coordinates u(k)ij and v(k)jj are recorded and determined on the calibration object with the help of the coordinate lines and the spatial coordinates x(k)j, x(k)ij, z(k)ij are determined, where z(k) corresponds to the respective calibration distance which is equal for all elements in the kth calibration plane. For all xij, a polynomial of the (n−1)th degree is formed in Ujj with the calibration values and likewise for y, j, and Zij, so that the calibration process that is to be carried out one time is concluded.

In measuring, for every point the indices I, j and the image coordinates ujj are recognized. With the ujj that are obtained, the spatial coordinates x, y, z are computed from the calibration polynomials for all elements into which a surface can then be fitted which approaches the actual surface of the test object. In this copied surface, by superimposition with the image of the test object, visible characteristics such as for instance damaged areas, tears, or corrosion surfaces, can then be designated and their size measured.

What is claimed is:

1. A method for measuring the topography of a test object comprising the steps of projecting a test pattern consisting of regularly arranged elements onto the surface of a test object, with the recording of an image of the test object with projected test pattern by means of a video camera placed at intervals along a base and with an evaluation of the position of the elements of the test pattern in the image of the test object parallactically displaced by the topography of the test object, where the elements of the test pattern are arranged along at least a first axial direction running at an angle to the base, wherein the angle is determined according to a dissolution power of the video camera, and wherein every element moves with parallactic displacement on its own displacement line running parallel to the projection of the base, said displacement line having no points in common with other displacement lines, and from the position of each element on its displacement line the spatial coordinates of a related point of the test object are determined, whereby the complete test pattern is made up of a limited number of locally bounded elements produced by laser projection in a reference plane, so that the reference plane is selected perpendicular to the optical axis of the video camera in the object space in a reference distance from the projection system, the system parameters of the test object are ascertained from the elements projected in the reference plane, calibration parameters are related to the elements in the reference plane and in projection planes at various distances therefrom, and are filed in a storage system, for measuring the topography, the individual elements are identified with respect to their position within the test pattern and the relevant spatial coordinates are calculated from their position in the image of the test pattern, taking into account the calibration parameters.

2. A method according to claim 1, characterized by a calibration in which the position of the elements of the test pattern with their spatial coordinates at different distances to a calibration object with coordinate grid is recorded and stored, so that the related spatial coordinates can be called up from a storage facility during measurement of a test object after identification of the element of the test pattern and determination of its position in the image of the test object.

3. A method according to claim 2, wherein the line of displacement that can be observed for identifying an element of the test pattern, and from which intermediate values of the displacement can also be obtained during the current measurement, is computed from the discrete spatial coordinates determined during the calibration.

4. A method according to claim 1, wherein the parameters of an appropriate spatial surface are determined to the determined spatial coordinates with the help of a mathematical algorithm, and in this surface characteristics can be spatially measured after they have been marked in the superimposition with the image of the test object.

5. A method according to claim 4, wherein the determined spatial surfaces are correlated with corresponding spatial surfaces that have been obtained for the same test object using other measurement methods including but not limited to ultrasound, computer tomography, or magnetic resonance.

6. An endoscope for measuring the topography of a test object comprising with a projection system for projecting an optically recognizable test pattern onto the surface of an object area that is to be measured and with an imagerecording system and image evaluation system for determining the parallactically displaced image coordinates of the test pattern in the object area that is to be measured, where the distance of the center points of the aperture diaphragms of the projection system and of the image-recording system forms a measurement basis, and the elements of the test pattern are positioned at regular intervals in at least one first axial direction and this axial direction is rotated relative to the vertical projection of the measurement basis by an angle alpha, wherein alpha is determined according to a dissolution power of the image-recording system at which the elements (Pii) of the test pattern, at a modification of the projection distance in the image of the test object, move on lines of displacement which have no points in common, wherein the complete test pattern consists of a limited number of locally bounded elements (Pii) that are produced by laser projection and that can be identified clearly with respect to their position inside the projected complete test pattern.

7. An endoscope according to claim 6, characterized in that a two-dimensional test pattern is provided in which a limited number of additional locally bounded elements (Pii) are positioned at regular intervals in a second axial direction and in the plane encompassed by both axial directions, where the second axial direction forms any desired angle 0<β[betas [<180 to the first axial direction.

8. An endoscope according to claim 7, characterized in that the Elements (P,j) of the test pattern form an n-m matrix with n columns and m rows, where the n columns are each distanced along the first axial direction by s and the m rows are each distanced along the second axial direction by t each.

9. An endoscope according to claim 8, wherein the distance a of the lines of displacement is subject to the formula a =t s (n2 s2+t2)−½ sin β(beta).

10. An endoscope as in claim 8, characterized in that said angle is oc, wherein oc =arc tan (t n~1 s~1).

11. An endoscope according to claim 7, wherein for departures of the projected test pattern from the regular arrangements of its elements (Pij) in a reference plane, an uncertainty factor of u <½. a applies.

12. An endoscope according to claim 6, wherein the test pattern consists of point-shaped and/or ringshaped elements (P,j).

13. An endoscope according to claim 6, wherein the test pattern has elements made up of crossed lines.

14. An endoscope as in claim 6, wherein a diffractive optical element (DOE) is used to create a test pattern in the projection system.

15. An endoscope as in claim 14, wherein the projection system is positioned so that it is adjustable.

16. An endoscope as in claim 14, wherein a light source associated with the projection system can be modulated in brightness and/or wavelength for illuminating the DOE.

17. An endoscope as in claim 16, wherein a laser is used as a light source.

18. An endoscope as in claim 17, wherein a laser diode (21) is used as a laser.

19. An endoscope as in claim 18, wherein a temperature measurement device is linked with the laser diode.

20. An endoscope as in claim 19, wherein the temperature measurement device is coupled with a device for temperature stabilization of the laser diode.

21. An endoscope as in claim ,6 wherein a video camera is used as a image recording system.

22. An endoscope as in claim 6, wherein a cold light source is used to illuminate of the test object.

23. An endoscope as in claim 6, wherein a control device is provided for alternating image recording with and without projected test pattern.

24. An endoscope as in a claim 6, wherein a computer with image evaluation software is used for control, image storage, and image evaluation.

25. An endoscope as in any one of claims 6 through 24, wherein the image recording system and the projection system are positioned on the distal end of the endoscope, so that the light source associate with the projection system is positioned on the proximal end of the endoscope and a fiberglass is used for light transmission.

26. An endoscope as in claim 6, characterized in that a control device is provided for alternating image recording with and without projected test pattern wherein the vertical projection of the measurement basis is rotated by the angle alpha relative to an image edge of the image recording system.

27. An endoscope for measuring the topography of a test object comprising with a projection system for projecting an optically recognizable test pattern onto the surface of an object area that is to be measured and with an image-recording system and image evaluation system for determining the parallactically displaced image coordinates of the test pattern in the object area that is to be measured, where the distance of the pupil midpoints of the projection system and of the image-recording system forms a test basis, characterized in that the test pattern consists of a limited number of elements (P,j), which are positioned at regular intervals in at least a first axial direction, where this axial direction is rotated by an angle alpha relative to the vertical projection of the test basis, and where the parameters are selected for the test pattern in such a way that the lines of displacement on which the elements (P,j) of the test pattern move upon a change in the projection distance in the image of the test object, have no common points and that the distance a of the lines of displacement correspond at least to the resolution power of the image-recording system for a separate depiction of the elements (P,j) of the test pattern.

28. An endoscope as in claim 27, wherein the equation a =t s (n2 s2+t2)−½ sin β(beta) is valid for the distance a of the lines of displacement, wherein the elements (P,j) of the test pattern form an n-m matrix with n columns and m rows, where the n columns are each distanced along the first axial direction by s and the m rows are each distanced along the second axial direction by t.

29. An endoscope as in claim 27, wherein an uncertainty, u<½° a, applies for departures of the projected test pattern from the regular arrangement of its elements (Pij) in a reference plane.

* * * * *